United States Patent [19]

Fischer

[11] Plant 4,308

[45] Sep. 26, 1978

[54] VIOLET PLANT NAMED VERA

[75] Inventor: Arnold W. Fischer, Fallbrook, Calif.

[73] Assignee: Geo. J. Ball, Inc., West Chicago, Ill.

[21] Appl. No.: 839,285

[22] Filed: Sep. 30, 1977

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Rummler and Snow

[57] ABSTRACT

A new and distinct variety of African violet plant for greenhouse culture and potted plant production distinguished by the purple violet coloration of its abundant flowers which are borne on strong upright peduncles and held well above a horizontally spreading abundance of variegated dark green leaves of a generally orbicular shape, the flower petals being of both light and dark coloring in each blossom and most having a fine white marginal edging, and the foliage having an attractive quilted velutinous texture which enhances the appearance of the flower mass.

1 Drawing Figure

BACKGROUND OF THE INVENTION

My new variety of African violet plant was discovered by me as a seedlling of unknown parentage grown among random pollinated plants cultivated by me at my breeding facilities at Hanover, Germany, with the object of developing novel flower coloring and improved growth characteristics and stamina for indoor potted plant culture. This new plant is much like the variety Rachel (U.S. Plant Pat. No. 4,113) in many respects, differing particularly in its coloration and for that reason was selected for propagation and testing. Propagation was carried on by me at Hanover, Germany, by means of leaf cuttings, through successive generations and demonstrated to me that the distinctive characteristics of this plant were holding true, appeared to be firmly fixed, and that this new variety was worthy of commercial exploitation. Accordingly propagation of this new variety of African violet is now being done at West Chicago, Ill., and at Woodburn, Oreg., U.S.A., by means of leaf cuttings and divisions of shoots.

DESCRIPTION OF THE DRAWINGS

This new variety of African violet plant is illustrated by the accompanying photographic drawing which shows, in full color, a potted plant of the new variety in full bloom and a series of the flowers in full face display to show variations of flower coloring that may occur on a single plant, the color rendition being as nearly true as it is reasonably possible to obtain by conventional professional photographic procedures.

DESCRIPTION OF THE NEW PLANT

The following is a detailed description of my new African violet plant based upon observations of greenhouse pot plants at West Chicago, Ill., during the Spring of 1977, the color designations being determined according to the R.H.S. Colour Chart published by The Royal Horticultural Society of London, England.

THE PLANT

Origin: Seedling.

Parentage: Unknown.

Classification:

*Botanic.*—*Saintpaulia ionantha.*

*Commercial.*—African Violet.

Form: Compact potted plant.

Height: About 1½ to 2 inches from soil to top of foliage and about 4 to 5 inches from foliage to top of the flowers.

Growth: Condensed and vigorous with very strong horizontally spreading petioles and sturdy upright peduncles.

Branching: Axillary branching can occur on older plants.

Foliage: Abundant with a variable number of leaves.

*Blade size of mature leaf.*—About 1½ to 2½ inches long and about 1¾ to 2½ inches wide.

*Leaf form.*—Orbicular with sagittate base, an acute to obtuse apex, and crenate margins.

*Texture.*—Velutinous.

*Venation.*—Pinnately veined. The veins are pronounced on the under side of the leaf.

*Color.*—Upper Side — Yellow-Green 147A with lighter green main vein and the marginal area of the leaf. Under Side — Greyed-Purple 186B with older leaves becoming Greyed-Green 194D. Main veins are Greyed-Red 182B with older leaves becoming Greyed-Green 194B.

*Petioles.*—About 2 to 4 inches long, averaging 3½ inches.

THE BUD

Form: Globular, becoming urn-shaped as bud opens.

Size: About ¼ to ⅜ inch in diameter, just prior to opening.

Rate of opening: 3 to 5 weeks from visual bud to opening.

Color:

*When sepals first divide.*—White 155A.

*When sepals begin to unfurl.*—Purple 79B to 79A.

Sepals: Hooded over bud for a short period.

*Shape.*—Spear-shaped and upstanding.

*Curlback.*—Slightly appressed to petals.

*Color.*—Greyed-Red 182B.

Calyx: Shape — funnel-shaped.

*Splitting.*—Calyx splits to star shape.

*Aspect.*—Smooth on inside; hairy on outside.

Peduncle: About 1¾ to 2¼ inches long, with a velutinous surface.

*Strength.*—Erect and exceptionally strong.

*Color.*—Greyed-Red 182B becoming green at the apex.

THE FLOWER

Blooming habit: Recurrent to continuous the year around, blooming more in Spring and Fall than in other periods.

Size: Medium to large.

*Diameter.*—About 1 to 1¾ inches, average 1¼ inch.

*Depth.*—About ¼ to ½ inch.

Shape: Cupped when bloom first opens becoming flattened as bloom matures.

Borne: The inflorescence is a cyme.

Petalage: Petals are basally connate.

*Number.*—5 when single with petaloid anthers to 10 when fully double with petaloid anthers.

*Arrangement.*—Gamopetalous.

*Form.*—Zygomorphic when single, with slightly wavy margin.

*Texture.*—Soft.

*Appearance.*—Glittery on upper side. Satiny on lower side.

*Color.*—Upper petals — Purple-Violet 82A to 83B with a more or less distinct White (155B) margin which may be up to 1/16 inch wide, depending on culture. Lower Petals — Purple-Violet 80B and 81B. Reverse Side — Uniform to mottled Purple-Violet 81B to 81C.

Petaloids: Number — 1 to 4 petaloid anthers.

*Size.*—About ¼ to ½ inch long. Average — ¼ inch.

*Color.*—Same as petals.

Peduncle: Length — 1¼ to 2½ inches. Average — 2 inches.

*Strength.*—Sturdy and upright.

*Color.*—Greyed-Red 182B becoming Greyed-Green at apex.

Discoloration, after full bloom: The white edging of the petals becomes less distinct.

Effect of weather: In hot weather, the color becomes less vivid and flower life is decreased.

Persistence: Flowers hang on and dry, turning brown at senescence.

Fragrance: None.

Lasting quality: 12 to 14 days as a fully opened flower.

REPRODUCTIVE ORGANS

Stamens:

*Anthers.*—Number — 2 when single, each with 2 anther cells, 4 when double, occasionally. Arrangement: Basifixed, connate at apex.

*Filaments.*—About 1/16 to ⅛ inch long. Color: White 155A with or without a purple blush.

*Pollen.*—Color — Yellow 7A.

Pistils: Number — One, occasionally two.

*Style.*—About ¼ to ⅜ inch long. Color: Green at base, purple at apex.

*Stigmas.*—Color — Purple-Violet.

Ovaries: Superior and velutinous.

Fruit: Normally none, except were special attempts have been made to pollinate the flower.

This variety of African violet most nearly resembles the variety Rachel (U.S. Plant Pat. No. 4,113) in most of its growth and blooming habits and characteristics, the main differences residing in flower coloration, the new plant having flowers of a purple-violet color whereas Rachel has violet-blue flowers. Other differences are found in the foliage shape and texture of the two plants, the new plant having leaves that tend to be more rounded at the apex and more guilted than the leaves of Rachel.

I claim:

1. A new and distinct variety of African violet plant substantially as herein shown and described, characterized by its purple-violet flowers, most petals of which are delicately edged with white.

* * * * *

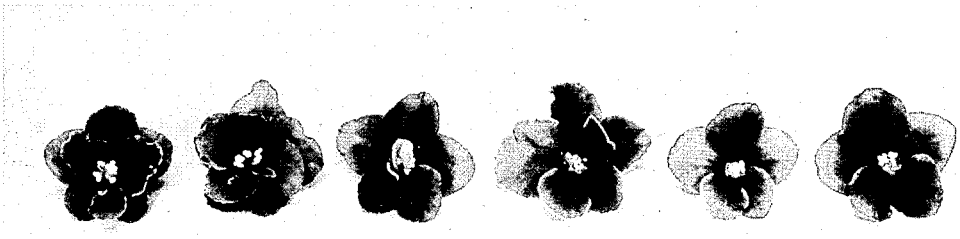

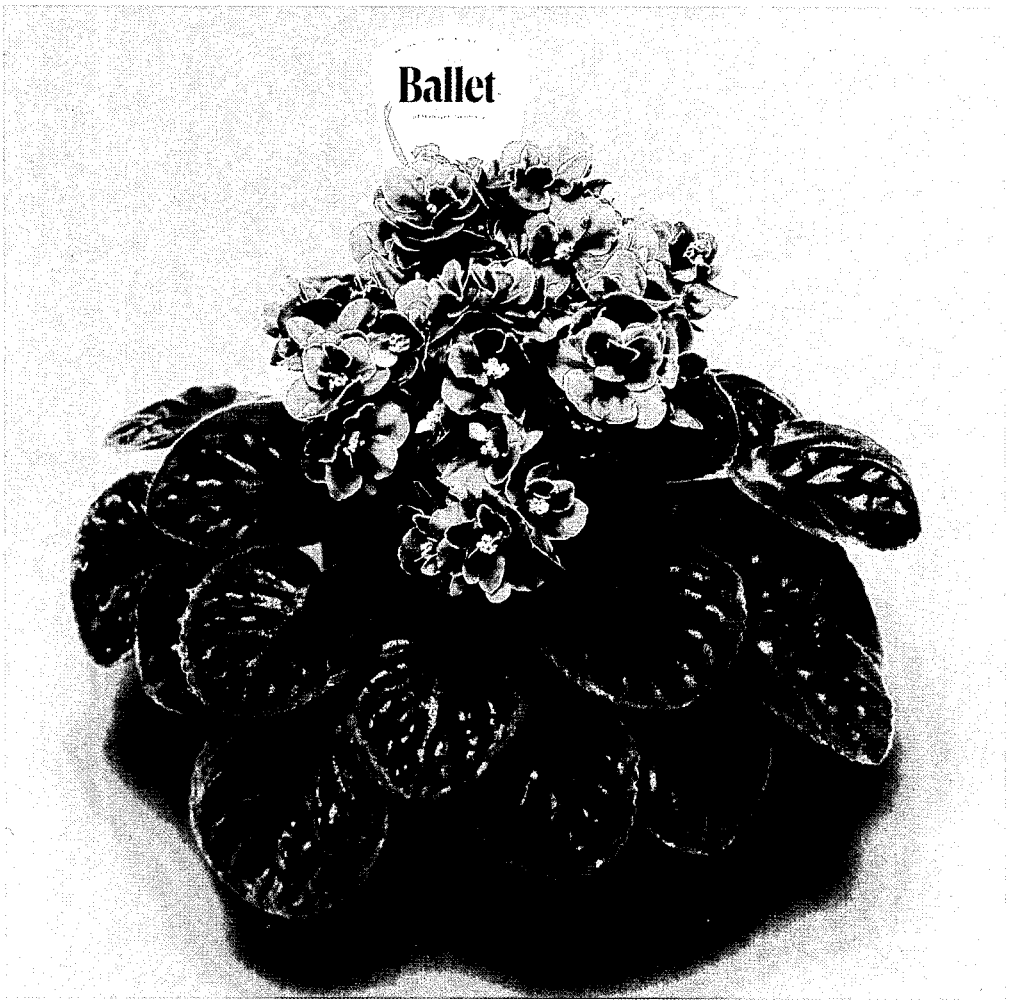
Ballet